United States Patent [19]

Bellani et al.

[11] Patent Number: 4,594,421
[45] Date of Patent: Jun. 10, 1986

[54] IMIDAZOPYRIDINE COMPOUNDS

[75] Inventors: Piero Bellani; Gaetano Clavenna; Alberta Sosio, all of Milan; Rinaldo Pellegrini, Carbonera, all of Italy

[73] Assignee: RBS Pharma (Roger Bellon Schoum) S.p.A., Milan, Italy

[21] Appl. No.: 696,589

[22] Filed: Jan. 31, 1985

[30] Foreign Application Priority Data

Feb. 2, 1984 [IT] Italy ................................ 19413 A/84

[51] Int. Cl.⁴ .......................................... C07D 487/04
[52] U.S. Cl. .................................... 546/121; 546/264
[58] Field of Search ............................................ 546/121

[56] References Cited

U.S. PATENT DOCUMENTS 4,096,264  6/1978  Bochis et al. ...................... 424/256
4,141,898  2/1979  Kuhla ................................. 546/121

Primary Examiner—Richard A. Schwartz
Assistant Examiner—Kurt G. Briscoe

[57] ABSTRACT

New imidazopyridine derivatives are described, having the following formula:

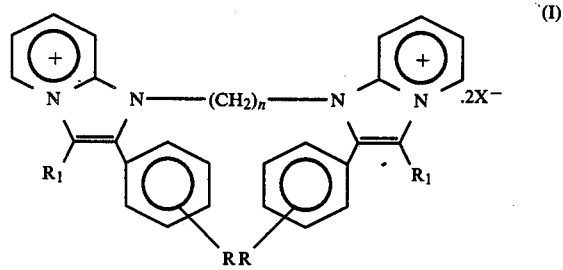

wherein R represents a hydrogen atom, an alkyl radical of 1 to 3 carbon atoms, a methoxy group or a halogen atom, $R_1$ represents a hydrogen atom, an alkyl radical of 1 to 3 carbon atoms, n represents an integer of 1 to 10, X represents a non-toxic pharmaceutically acceptable ion, which possess a skeletal muscle paralyzing activity.

5 Claims, No Drawings

IMIDAZOPYRIDINE COMPOUNDS

SUMMARY OF THE INVENTION

The object of the present invention is a new class of imidazopyridine compounds having an interesting pharmacological activity.

More precisely, the compounds of the invention have the following structural formula:

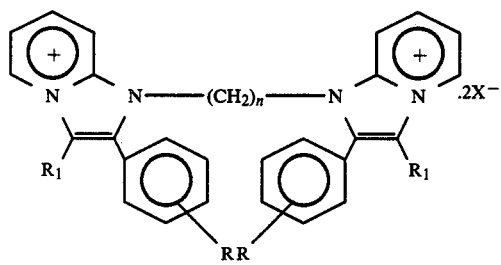

wherein R represents a hydrogen atoms, an alkyl radical of 1 to 3 carbon atoms, a methoxy group or a halogen atom, $R_1$ represents a hydrogen atom, an alkyl radical of 1 to 3 carbon atoms, n represents an integer of 1 to 10, X represents a pharmaceutically acceptable ion.

The abovementioned compounds (I) possess skeletal muscle paralysing activity, which develops through the block of nervous impulse transmission at the level of the skeletal neuromuscular junction.

BACKGROUND OF THE INVENTION

Drugs with this property are classified, either as blockers of competitive type, if they compete with ACh on cholinergic receptors situated on the post-junctional membrane, or as blockers of depolarizing type, if the neuromuscular block is preceded by depolarization of the membrane. Moreover, agents provided with a combined competitive and depolarizing action are known, even if scarcerly used in therapy.

Drugs provided with skeletal muscle paralysing activity are clinically used, especially in anaesthesiology.

Skeletal muscle paralysing agents of the depolarizing type are mainly provided with fast starting and shortly lasting action. That makes them suitable for many therapeutic uses, even if it is known they may show serious complications, such as arrhythmias, cardiac arrest and, frequently, post-surgery muscular pains, just because of their mechanism of action, which causes muscular fasciculation before the effect of neuromuscular block starts.

The skeletal paralysing agenst of competitive type do not show the unwanted side effects, which may arise when using depolarizing blocking agents, but they are characterized by a slow onset and a long lasting duration of action. Moreover, they could induce unwanted side effects, such as release of histamine, ganglionic block, muscarinic receptor block (mainly, cardiac receptors) and inhibition of the norepinephrine reuptake; which effects could also induce relevant interference with the autonomic control of circulation.

DETAILED DESCRIPTION OF THE INVENTION

It has now been found that the new compounds of formula (I) possess a competitive neuromuscular blocking activity, whose paralysing action promptly arises is short lasting and, at active doses, does not detectably interfere with the cardiovascular system.

The compounds of the present invention have been pharmacologically studied, using as a standard fazadinium bromide, i.e. 1,1-azabis 3-methyl-2-phenylimidazo 1,2-a pyridinium bromide, a known compound of the commerce, provided with a competitive skeletal muscle paralysing activity.

The neuromuscular blocking activity has been evaluated:

in vitro, using the phrenic-diaphragm preparation according to the method described by Bülbring E. (Brit. J. Pharmac. Chemother. 1, 38, 1946). The preparation, taken from male Sprague-Dawley rats weighing 200–250 g, was placed into a bath for isolated organs, thermostatically kept at 37° C. and containing a nutritional liquid oxygenated with 5% carboxygen. The phrenic nerve was stimulated by means of square wave impulses (12 per min., duration 0.5 msec., overmaximal voltage). All compounds under examination and the reference standard were added to the bath at cumulative concentrations and showed to be active. The dose-effect curve, determined for each of them, allowed to calculate the $EC_{50}$ or effective concentration able to reduce the muscular contraction of 50% (Table 1);

in vivo, using the sciatic-gastrocnemious preparation, substantially following the method described by Hughes R. (Br. J. Anaesth. 44, 27, 1972). Male Sprague-Dawley rats weighing 200–250 g, anaesthetized (urethane 1,2 g/kg i.p.) and submitted to forced ventilation, were treated. The sciatic nerve was stimulated at a rate of 6 impulses per min. by means of square waves and overmaximal voltage with a duration of 0.5 msec. The left carotid artery was incannulated for the continuous registration of arterial blood pressure and heart rate.

The compounds to be tested were administered by i.v. route at increasing doses, given at intervals of at least 30 min. from one to another and, in any case, after the effect of previous administration had completely exhausted.

All compounds under examination and the fazadinium bromide showed to be active, so that it was possible to draw for each of them the dose-effect curve that allowed to calculate the $ED_{50}$ (effective dose causing the 50% reduction of muscular contraction) listed in Table 2. In addition, the time of latence (the interval between the administration and the maximal effect) and that of complete recovery have been determined. The percentage variations of arterial blood pressure and heart rate at $ED_{50}$ on muscular contraction are reported in Table 2.

In addition to the study on rat, the compounds under examination were administered by i.v. route to seven-day-old chicks in order to observe what type of paralysis (flaccid or spastic) had been induced. All compounds under examination have caused flaccid paralysis, showing that their mechanism of action is of a non-depolarizing type.

Acute toxicity or $LD_{50}$ was determined in male Sprague-Dawley rats weighing 1.2 g/kg i.p. The compounds under examination were administered by i.v. route at different level doses (5 animals for each dose). The $LD_{50}$ were then calculated according to the method of Litchfield J. T. and Wilcoxon F. J. (J. Pharmac. Exp. Ther., 95, 99, 1949). The results obtained are reported in Table 3.

The compounds of the invention can be dissolved in suitable solvents making them suitable to the administration, which is generally performed by parenteral, intravenous or intramuscular route. The pharmaceutical compositions can be formulated in a way suitable to single or multiple dosage depending on their specific use.

TABLE 1

| Neuromuscular blocking activity "in vitro". | |
|---|---|
| Compound | EC$_{50}$ ($\mu$M/l) |
| Example 10 | 31.4 |
| Example 9 | 28.9 |
| Example 11 | 12.9 |
| Example 2 | 11.9 |
| Example 12 | 115.2 |
| Example 4 | 28.7 |
| Example 8 | 13.6 |
| Example 3 | 14.3 |
| Example 7 | 15.4 |
| Example 5 | 14.7 |
| Example 1 | 15.0 |
| Fazadinium bromide | 13.9 |

TABLE 2

Neuromuscular blocking activity "in vivo" and cardiovascular effects

| | Neuromuscular block | | | Cardiovascular effects | |
|---|---|---|---|---|---|
| Compound | ED$_{50}$ ($\mu$g/kg i.v.) | Latence (min.) | Recovery (min.) | Arterial blood pressure Δ % | Heart rate Δ % |
| Example 10 | 4.0 | 2.8 | 14.0 | −30 | +28 |
| Example 9 | 3.3 | 2.1 | 7.0 | −31 | +25 |
| Example 11 | 2.1 | 2.3 | 8.8 | −40 | +42 |
| Example 2 | 1.9 | 2.2 | 9.2 | −45 | +22 |
| Example 12 | 5.6 | 2.6 | 12.2 | −5$^{(a)}$ | +6 |
| Example 4 | 5.0 | 1.3 | 6.2 | −28 | +1 |
| Example 8 | 1.3 | 2.1 | 7.7 | −40 | +68 |
| Example 3 | 1.6 | 1.2 | 5.0 | −28 | +40 |
| Example 7 | 3.0 | 1.5 | 9.8 | −50 | −8 |
| Example 5 | 1.9 | 1.5 | 6.4 | −39 | +26 |
| Example 1 | 3.0 | 2.2 | 7.9 | −37 | +28 |
| Fazadinium bromide | 1.0 | 1.5 | 6.6 | −16 | +30 |

$^{(a)}$—24% at minimal active dose on muscular contraction.

TABLE 3

| Acute toxicity in rat. | |
|---|---|
| Compound | LD$_{50}$ ($\mu$M/kg i.v.) |
| Example 10 | 8.8 |
| Example 9 | 3.2 |
| Example 11 | 3.1 |
| Example 2 | 2.7 |
| Example 12 | 9.7 |
| Example 4 | 4.3 |
| Example 8 | 2.0 |
| Example 3 | 2.0 |
| Example 7 | 6.0 |
| Example 5 | 2.6 |
| Example 1 | 3.9 |
| Fazadinium bromide | 1.5 |

The compounds of the present invention may be prepared by reacting under heating a bis-(2-pyridylamino)alkylene (IV) optionally substituted with an α-halo-acylbenzene (III), in a suitable polar solvent, particularly an alcohol with low boiling point, and then dehydrating in acid conditions the imidazopyridinium derivative so obtained.

Schematically the process may be indicated as follows:

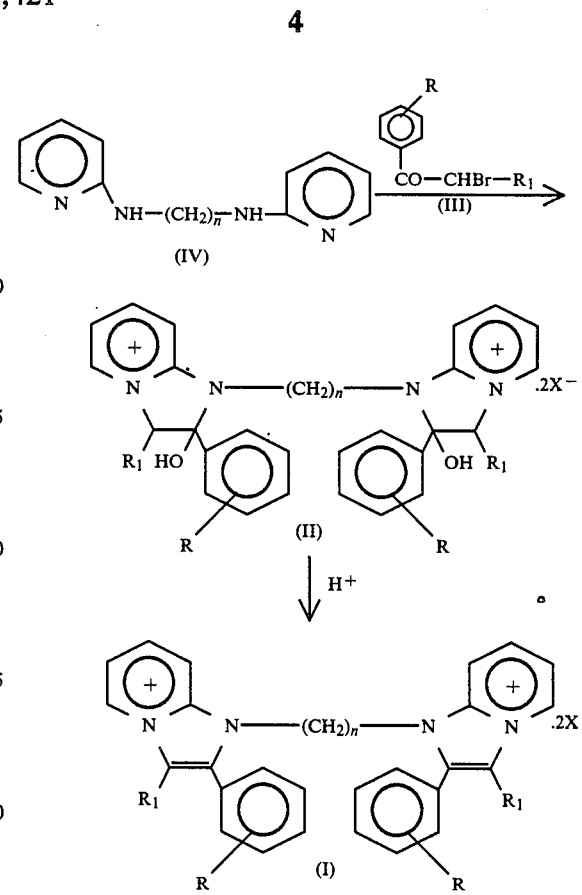

wherein R, R$_1$, n and X have the above mentioned meanings.

The reaction for building the imidazolic ring usually is carried out at a temperature between 60° and 120° C. and in practice the intermediate compound II may not be isolated and the reaction may proceed until the formation of the final compound I.

The intermediate compounds II are new compounds themselves and show to be pharmacologically active.

EXAMPLE 1

1,1'-(1,6-Hexamethylene)bis[2-(4'-fluoro)phenyl-]imidazo[1,2-a]pyridinium perchlorate A mixture consisting of 2.0 g of 1,6-bis(2-pyridylamino)hexane and 3.24 g α-chloro-p.fluoroacetophenone and 60 ml of 96% ethyl alcohol is refluxed for 16 hours and then 4.0 ml of 70% perchloric acid is added thereto and the mixture is heated at the boiling point for 2 hours. Cooling at room temperature and filtration gives 2.45 g 1,1'-(1,6-hexamethylene)bis[2-(4'-fluoro)phenyl]imidazo[1,2-a]pyrdidinium perchlorate, which, after recrystallization from acetonitryle, melts at 262°–265° C.

Analysis: found: C=53.99%; H=4.62%; N=7.82%. C$_{32}$H$_{30}$F$_2$N$_4$.2ClO$_4^-$ requires: C=54.32%; H=4.27%; N=7.92%.

EXAMPLE 2

1,1'-(1,8-Octamethylene)bis-2-phenylimidazo[1,2-a]piridinium perchlorate

The process is similar to that described in Example 1, starting from 1,8-bis(2-pyridylamino)octane and α-bromoacetophenone to obtain with a yield of 56%, 1,1-(1,8-octamethylene)bis-2-phenylimidazo[1,2-a]pyridinium perchlorate, which melts at 204°-205° C.

Analysis: found: C=57.64%; H=5.21%; N=7.84%; $C_{34}H_{36}N_4.2ClO_4^-$ requires: C=58.37%; H=5.19%; N=8.01%.

EXAMPLE 3

1,1'-(1,8-Octamethylene)bis(2-phenyl-3-methyl-)imiadazo[1,2-a]pyridinium perchlorate The process is similar to that described in Example 1, starting from 1,8-bis(2-pyridylamino)octane and α-bromopropiophenone to obtain, with a 30%, 1,1'-(1,8-octamethylene)bis(2-phenyl-3-methyl)imidazo-[1,2-a]pyridinium perchlorate, which melts at 203°-205° C.

Analysis: found: C=59.82%; H=5.41%; N=7.92%; $C_{36}H_{40}H_4.2ClO_4^-$ requires: C=59.42%; H=5.54%; N=7.70%.

EXAMPLE 4

1,1'-(1,4-Tetramethylene)bis(2-phenyl-3-methyl-)imidazo[1,2-a]pyridinium perchlorate The process is similar to that described in Example 1, starting from 1,4-bis(2-pyridylamino)butane and α-bromopropiophenone to obtain, with a 29% yield, 1,1'-(1,4-tetramethylene)bis(2-phenyl-3-methyl)imidazo[1,2-a]pyridinium perchlorate, which melts at 302°-304° C.

Analysis: found: C=56.95%; H=4.82%; N=8.12%; $C_{32}H_{32}N_4.2ClO_4^-$ requires: C=57.24%; H=4.80; N=8.34%.

EXAMPLE 5

1,1'-(1,6-Hexamethylene)bis[2-(4'-methoxy)phenyl-]imidazo[1,2-a]pyridinium bromide monohydrate A mixture consisting of 1.0 g of 1,6-bis(2-pyridylamino)hexane, 2.16 g of α-bromo-p.metoxyacetophenone and 30 ml of 96% ethyl alcohol is refluxed for 4 hours and then 2.0 ml of 47% bromidric acid are added and the mixture is heated at the boiling point for a further 2 hours. The solvent is evaporated and the residue suspended in water, adjusted to pH 7 by addition of sodium hydroxide and filtered to give 2.0 g of 1,1'-(1,6-hexamethylene)bis[2-(4'-methoxy)phenyl-]imidazo[1,2-a]pyridinium bromide monohydrate -elting at 281°-283° C. and, after crystallization from water, at 282°-284° C.

Analysis: found: C=57.17%; H=5.21%; N=7.82% $C_{34}H_{36}N_4O_2.2Br^-.H_2O$ requires: C=57.48%; H=5.39%; N=7.89%.

EXAMPLE 6

1,1'-(1,8-Octamethylene)bis-2-phenylimidazo[1,2-a]pyridinium bromide trihydrate

The process is similar to that described in Example 5, starting from 1,8-bis(2-pyridilamino)octane and α-bromoacetophenone to obtain, with a 55% yield, 1,1'-(1,8-octamethylene)bis-2-phenylimidazo[1,2-a]pyridinium bromide trihydrate, which melts at 100°-110° C.

Analysis: found: C=56.85%; H=5.76%; N=7.32%. $C_{34}H_{36}N_4.2Br^-.3H_2O$ requires: C=57.15%; H=5.92%; N=7.83%.

EXAMPLE 7

1,1'-(1,6-Hexamethylene)bis[2-(4-bromophenyl)-]imidazo[1,2-a]pyridinium bromide

The process is similar to that described in Example 5, starting from 1,6-bis(2'-pyridylamino)hexane and α,p-dibromoacetophenone, to obtain, with a 45% yield, 1,1'-(1,6-hexamethylene)bis-[2-(4-bromophenyl)-]imidazo[1,2-a]pyridinium bromide, melting at 268°-273° C.

Analysis: found: C=48.66%; H=3.66%; N=7.20%; $C_{32}H_{30}Br_2N_4.2Br^-.3H_2O$ requires: C=48.66%; H=3.83%; N=7.09%.

EXAMPLE 8

1,1'-(1,6-Hexamethylene)bis(2-phenyl-3-methyl-)imidazo[1,2-a]pyridinium perchlorate A mixture consisting of 2 g of 1,6-bis(2-pyridylamino)hexane, 3.92 g of α-bromopropiophenone and 100 ml 96% ethyl alcohol, is refluxed for 60 hours. After evaporating the solvent, the residue is taken up with acetone and filtered to give 1,85 g of 1,1'-(1,6-hexamethylene)bis(2-phenyl-2-hydroxy-3-methyl-2,3-dihydro)imidazo[1,2-a]pyridinium bromide melting at 145°-150° C. (yield 36%). After crystallization from isopropanol/ethyl acetate the solid melts at 151°-154° C.

Grams 1.85 of 1,1'-(1,6-hexamethylene)bis(2-phenyl-2-hydroxy-3-methyl-2,3-dihydro)imidazo[1,2-a]pyridinium bromide are dissolved in 30 ml water.

After heating to boiling temperature, 20 ml 70% perchloric acid are added and it is refluxed for 30'. By cooling to room temperature and filtration of the solid precipitate, 1,13-(1,6-hexamethylene)bis(2-phenyl-3-methyl)imidazo[1,2-a]pyridinium perchlorate melting at 235°-240° C. is obtained with a 85% yield. After crystallization from 90% ethanol, the solid melts at 249°-250° C.

Analysis: found C=58.62%; H=5.07%; N=8.14% $C_{34}H_{36}N_4.2ClO_4^-$ requires: C=58.37%; H=5.19%; N=8.01%.

EXAMPLE 9

1,1'-(1,4-Tetramethylene)bis-2-phenylimidazo[1,2-a]pyridinium perchlorate

The process is similar to that described in Example 8, starting from 1,4-bis(2-pyridylamino)butane and α-bromoacetophenone to obtain at first, with a 34% yield, 1,1'-(1,4-tetramethylene)bis(2-hydroxy-2-phenyl-2,3-dihydro)imidazo[1,2-a]pyridinium bromide melting at 234°-236° C. and then, with a 87% yield, 1,1'-(1,4-tetramethylene)bis-2-phenylimidazo[1,2-a]pyridinium perchlorate melting at 275°-277° C. and, after crystallization from 70% ethyl alcohol, at 278°-279° C.

Analysis: found: C=55.09%; H=4.54%; N=8.35% $C_{30}H_{28}N_4.2ClO_4^-$ requires: C=56.00%; H=4.39%; N=8.71%.

EXAMPLE 10

1,1'-(1,2-Ethylene)bis-2-phenylimidazo[1,2-a]pyridinium perchlorate

The process id similar to that described in Example 8, starting from 1,2-bis(2-pyridylamino)ethane and α-bromoacetophenone to obtain at first, with a 30% yield, 1,1'-(1,2-ethylene)bis(2-hydroxy-2-phenyl-2,3-dihydro)imidazo[1,2-a]pyridinium bromide meltint at 246°–248° C. and then, with a 90% yield, 1,1'-(1,2-ethylene)bis-2-phenylimidazo[1,2-a]pyridinium perchlorate melting at 308°–310° C. and, after crystallization from water, at 312°–314° C.

Analysis: found; C=54.04%; H=3.84%; N=8.99% $C_{28}H_{24}N_4.2ClO_4^-$ requires: C=54.65%; H=3.93%; N=9.10%.

EXAMPLE 11

1,1'-(1,6-Hexamethylene)bis-2-phenylimidazo[1,2-a]pyridinium perchlorate

The process is similar to that described in Example 8, starting from 1,6-bis(2-pyridylamino)hexane and α-bromoacetophenone to obtain at first, with a 40% yield, 1,1'-(1,6-hexamethylene)bis(2-hydroxy-2-phenyl-2,3-dihydro)imidazo[1,2-a]pyridinium bromide, which by addition of sodium perchlorate in water it formes the corresponding perchlorate melting at 216°–225° C. and then, with a 90% yield, 1,1'-(1,6-hexamethylene)bis-2-phenylimidazo[1,2-a]pyridinium perchlorate melting at 222°–234° C. and, after crystallization from 90% ethyl alcohol, at 226°–228° C.

Analysis: found: C=57.29%; H=4.86%; N=8.29% $C_{32}H_{32}N_4.2ClO_4^-$ requires: C=57.23%; H=4.80%; N=8.34%.

EXAMPLE 12

1,1'-(1,2-Ethylene)bis(2-phenyl-3-methyl)imidazo[1,2-a]pyridinium perchlorate The process is similar to that described in Example 8, starting from 1,2-bis(2-pyridylamino)ethane and α-bromopropiophenone to obtain at first 1,1'-(1,2-ethylene)bis(2-phenyl-2-hydroxy-3-methyl-2,3-dihydro)imidazo[1,2-a]pyridinium bromide and then 1,1'-(1,2-ethylene)bis(2-phenyl-3-methyl)imidazo[1,2-a]pyridinium perchlorate, which, after crystallization from 80% ethyl alcohol, melts at 310°–312° C.

Analysis: found: C=55.88%; H=4.50%, N=8.20%; $C_{30}H_{28}N_4.2ClO_4^-$ requires: C=56.00%; H=4.39%; N=8.71%.

EXAMPLE 13

1,1'-(1,6-Hexamethylene)bis(3-ethyl-2-phenyl)imidazo[1,2-a]pyridinium perchlorate The process is similar to that described in Example 8, starting from 1,6-bis(2-pyridylamino)hexane and α-bromobutyrophenone to obtain at first 1,1'-(1,6-hexamethylene)bis(3-ethyl-2-phenyl-2-hydroxy-2,3-dihydro)imidazo[1,2-a]pyridinium bromide and then 1,1'-(1,6-hexamethylene)bis(3-ethyl-2-henyl)imidazo[1,2-a]pyridinium perchlorate melting at 235°–236° C.

Analysis: found: C=58.68%; H=5.50%; N=7.70%; $C_{36}H_{40}N_4.2ClO_4^-$ requires: C=59.42%; H=5.54%; N=7.70%.

What we claim is:

1. An imidazopyridine derivative of structural formula:

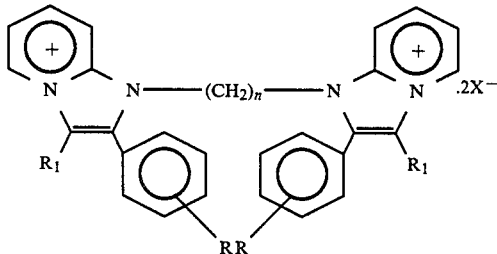

wherein R represents a hydrogen atom, an alkyl radical of 1 to 3 carbon atoms, a methoxy group or a halogen atom, $R_1$ represents a hydrogen atom, an alkyl atom of 1 to 3 carbon atoms, n represents an integer 1 to 10, X represents a non-toxic pharmaceutically acceptable ion.

2. 1,1'-(1,6-Hexamethylene)bis[2-(4'-bromophenyl)-]imidazo[1,2-a]pyridinium bromide.

3. 1,1'-(1,2-Ethylene)bis(2-phenyl-3-methyl)imidazo[1,2-a]pyridinium perchlorate.

4. 1,1'-(1,2Ethylene)bis-2-phenylimidazo[1,2-a]pyridinium perchlorate.

5. 1,1'-(1,6-Hexamethylene)bis-2-phenylimidazo[1,2-a]pyridinium perchlorate.

* * * * *